United States Patent [19]

Courbon

[11] 4,152,923

[45] May 8, 1979

[54] APPARATUS FOR SELECTIVELY SAMPLING DUST AND LIKE SOLID PARTICLES GRANULOMETRICALLY

[75] Inventor: Paul Courbon, Apremont, France

[73] Assignee: Carbonnages de France, Paris, France

[21] Appl. No.: 898,886

[22] Filed: Apr. 21, 1978

[30] Foreign Application Priority Data

Apr. 25, 1977 [FR] France .............................. 77 12364

[51] Int. Cl.² ............................................ G01N 15/06
[52] U.S. Cl. .......................................... 73/28; 55/270
[58] Field of Search .............. 73/28, 421.5 R, 432 PS; 55/270

[56] References Cited

U.S. PATENT DOCUMENTS

| 3,590,629 | 7/1971 | Courbon | 73/28 |
| 3,765,155 | 10/1973 | Courbon | 73/28 |
| 3,949,594 | 4/1976 | Treaftis et al. | 73/28 |

Primary Examiner—Stephen A. Kreitman
Attorney, Agent, or Firm—Cushman, Darby & Cushman

[57] ABSTRACT

The invention relates to apparatus for the selective sampling of dust or other solid particles granulometrically.

A rotor is composed of a cup 6 containing a ring of porous foam 7 provided with a central air supply duct 8 and an aperture 17 surmounted by a casing 15 which, opposite the aperture 17, is provided with an aperture 18 into which leads a central annular suction duct 14. Dust particles larger than 5μ are collected in the casing 15, while finer dust particles are collected in the foam 7.

The invention is applicable to the sampling of dust by making a granulometric cut.

4 Claims, 1 Drawing Figure

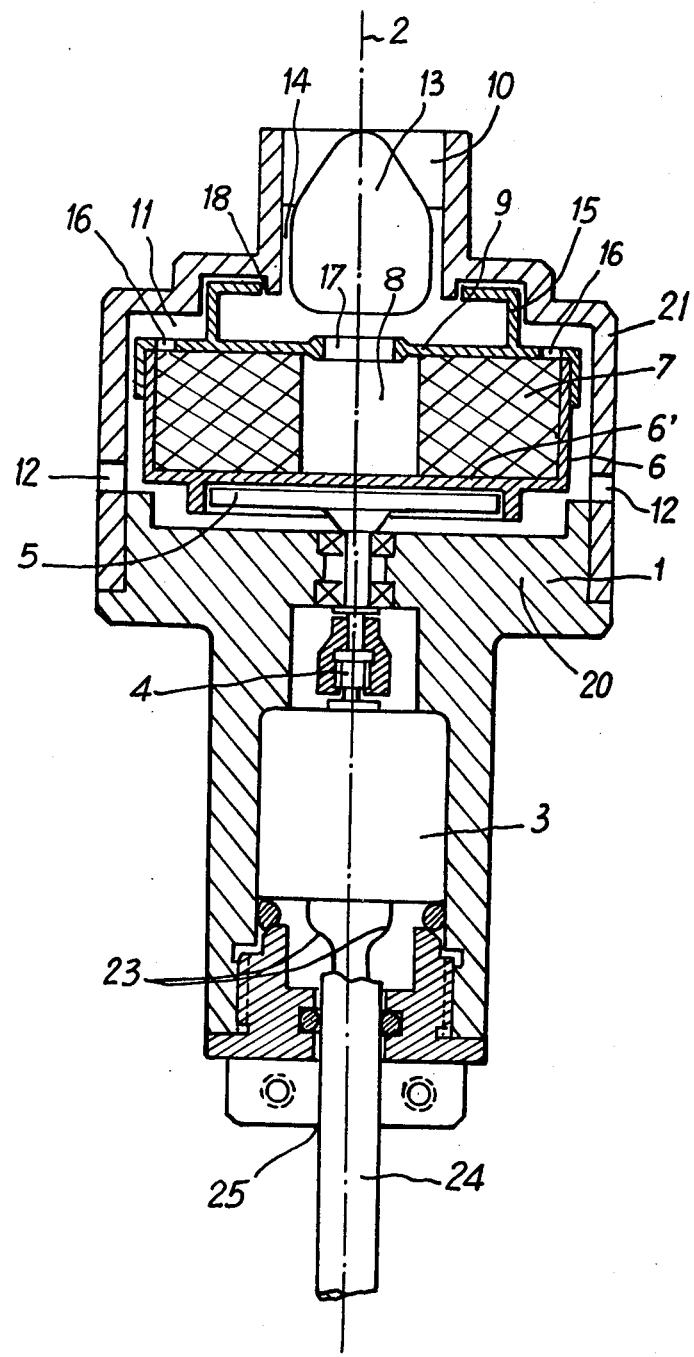

APPARATUS FOR SELECTIVELY SAMPLING DUST AND LIKE SOLID PARTICLES GRANULOMETRICALLY

FIELD OF THE INVENTION

The present invention relates to apparatus for the selective sampling, in accordance with a granulometric cut, of dust and like solid particles suspended in a gaseous medium, such as the atmosphere.

DISCUSSION OF THE PRIOR ART

Devices for the sampling of dust suspended in the air are known, particularly from U.S. Pat. No. 3,765,155 which comprises a rotor constituted in part by a rotary element made of a material permeable to air and having a central supply duct provided with a central suction aperture. The rotary element is rotationally fastened to a support plate impermeable to air and rotates at high speed inside a circular sampling chamber provided with a central suction duct coaxial to the rotating element and with at least one peripheral evacuation aperture.

The purpose of an apparatus of this kind is to take samples of dust or like solid particles from the atmosphere for examination and analysis. An apperatus of this kind therefore effects total sampling with the sole exception of dust which is too fine to be retained by the permeable material, the latter generally being a foam material having communicating pores. In the analysis of the respiratory risk to a human being by reason of his exposure to a polluted atmosphere it is sometimes important to measure the total dust content of the atmosphere which indicates the possible discomfort to the human being. In addition, it is often required to measure the portion of dust particles in the atmosphere which are capable of reaching the alveoli of the lungs of the human being and to estimate their noxiousness. It is generally accepted that the cut made by natural filtration by the upper respiratory tracts of a human being (nose, mouth, trachea, bronchi) is at about $5\mu$.

It is an aim of the present invention to propose a sampling apparatus which permits measurement on the one hand of the atmospheric concentration of dust particles smaller than $5\mu$ and on the other hand the total atmosphere concentration of dust or, what amounts to the same thing, the concentration of dust particles larger than $5\mu$.

SUMMARY OF THE INVENTION

According to the present invention there is provided apparatus for the selective sampling, in accordance with a granulometric cut, of dust and like solid particles suspended in a gaseous medium, comprising a rotor mounted for rotation at high speeds within a circular sampling chamber having at least one peripheral evacuation orifice and a central annular suction duct coaxial with the rotor, the rotor comprising a thick rotary element of a material permeable to the gaseous medium rotationally fixed to a support plate which is impermeable to the gaseous medium, the rotary element defining a central supply duct having a central suction aperture whose diameter is substantially less than the internal diameter of the annular suction duct, wherein the rotor further comprises a circular collection casing coaxial with and at least partly covering the rotary element with the exception of the central suction aperture, the collection casing having, on its side nearer to the annular duct, a circular aperture whose diameter is at least equal to the external diameter of the annular duct.

Through suitable adaptation of the diameters and of the speed of rotation of the elements of the apparatus there is thus effected retention of dust particles larger than $5\mu$ (or than any other selected value) in the circular collection casing where they are first retained by impact against the bottom of the circular casing, in which through friction they receive a centrifugal impulse directing them towards the circular periphery of the casing, where finally they are retained through centrifugal force. On the other hand the streams of air drive the dust particles smaller than $5\mu$ into the central supply duct of the thick rotary element, where they are retained.

It is advantageous for the face of the casing which at least partly covers the rotary element to be provided with a central circular aperture whose diameter is substantially smaller than the diameter of the central supply duct of the rotary element, this central aperture constituting the aperture of the central supply duct of the rotary element.

It is also advantageous for the central annular suction duct, which is composed of a tube in which a bulb is centrally located, to lead into the circular casing at a point opposite to the central opening provided in the face of the said casing.

BRIEF DESCRIPTION OF THE DRAWINGS

An embodiment of the present invention will hereinafter be described, by way of example, with reference to the accompanying drawings, in which the single FIGURE illustrates diagrammatically in axial section an apparatus according to the invention.

DESCRIPTION OF A PREFERRED EMBODIMENT

The apparatus comprises a casing 1 of generally circular shape having an axis 2. Inside the casing 1 is housed a motor 3 whose output shaft 4, which is coaxial with the axis 2, drives a driving plate 5. The driving plate 5 magnetically rotates a cup 6 having a rigid, impermeable base which constitutes a support plate for a thick ring 7 of open-pore foam, for example of polyurethane, which is provided with a central supply duct 8 having an opening 9 facing a central suction duct 10 disposed axially in the casing 1. The cup 6 carrying the foam ring 7 together form the frame of a rotor arranged to rotate in an annular chamber 11 provided in the upper part of the casing 1. As is known, the casing 1 is also provided with evacuation vents 12 for air which has passed through the apparatus. A cable 24 for supplying current to the motor 3 by way of two electric conductors 23 passes through an opening 25 at the base of the casing 1.

The central suction duct 10 has a central bulb 13 delimiting an annular duct 14 between the bulb 13 and the inner wall of the duct 10.

Above the foam ring 7 the cup 6 receives a circular casing 15 the base of which closes the cup, covering it after the style of a lid. The base of the casing 15 has vents 16 for the evacuation of air sucked into the rotor. These vents 16 could equally well be provided in the side walls of the cup 6. The base of the casing 15 is provided with a circular central aperture 17 whose diameter is substantially smaller than the diameter of the supply duct 8 of the foam ring 7. This aperture 17 serves as an opening to the duct 8. The external diameter of the bulb 13 is greater than that of the circular central aperture 17. In addition, on its side nearer to the annular duct 14 the casing 15 has another circular aperture 18 whose diameter is at least equal to the external diameter of the annular duct 14, that is to say to the internal diameter of the duct 10.

In order to make the apparatus more compact, the annular duct 14 extends directly into the interior of the casing 15 through the aperture 18 opposite the aperture 17.

In order to permit the dismantling of the apparatus and the recovery of the sampled dust from the casing and from the thick rotor, as well as the replacement of the latter, the chamber 11 is defined within an assembly comprising a support 20 on which is detachably fixed a cap 21 corresponding in shape, although larger to provide clearance, with the rotor composed of the parts 6, 7 and 15. The cap 21 is provided with the duct 10 together with the bulb 13 and also the vents 12 for the evacuation of air drawn in.

After the style of a fan, rotation of the rotor at high speed (7000 to 10000 revolutions per minute) produces the suction necessary for drawing air into the apparatus.

The dust-laden air drawn in through the annular duct 14 penetrates into the casing 15 in the form of an annular jet, is then diverted towards the central suction aperture 17, passes through the polyurethane foam filter 7, passes out through the peripheral vents 16, and returns to the atmosphere through the peripheral vents 12 in the casing 1.

The larger "non-breathable" particles carried by the air drawn in are not diverted towards the central aperture 17. Because of their inertia, these larger particles leave the diverted annular jet of air and move towards the bottom of the casing 15, where they are subjected to two mechanisms: an impact effect and an effect of re-entrainment through the torroidal, swirling flow due to the rotation of the rotor. They are then thrown onto the inside peripheral wall of the casing 15, where they are fixed through the action of centrifugal force.

The smaller breathable particles follow the stream of air and penetrate into the cup 6 containing the filter 7 of polyurethane foam in which they are trapped. Measurement can then be made by separately weighing the cup 6 containing the foam 7 and its casing 15. From the difference in weight before and after sampling, the cup 6 gives the weight of breathable dust collected whilst the casing 15 gives the weight of the coarser dusts. The volume of air being filtered being known, the respective concentrations at the sampling site can be deduced therefrom.

Thus, with an apparatus in which the cup 6 has a diameter of 35 mm and a speed of rotation of 8000 revolutions per minute and a flow of 600 liters per hour, a mean cut level of $3\mu$ is obtained. By taking suspended carbon dust from the air a collection rate of 70% of dust normally arrested by the upper respiratory tracts in the body is obtained, together with a collection rate of 30% of dust which normally penetrate into the air-cells of the lungs and are deposited therein.

Other adjustments are possible if the speed of rotation of the calibres of the inlet or outlet apertures are modified.

In one version the apparatus may be adapted for human use and be carried by a worker at his work station as an individual dust sampler, because of its small dimensions, low weight, and tested strength.

In another version it may be used for measuring particulate pollution of the atmosphere with the separation of breathable dusts from those which are normally arrested by the upper respiratory tracts.

I claim:

1. Apparatus for the selective sampling, in accordance with a granulometric cut, of dust and like solid particles suspended in a gaseous medium, said apparatus comprising:

a circular sampling chamber, at least one evacuation orifice communicating with said chamber through the periphery thereof, and an annular suction duct communicating with the chamber centrally thereof; and a rotor mounted in said sampling chamber for rotation at high speeds, said rotor comprising a support plate impermeable to the gaseous medium, and a thick rotary element of a material permeable to the gaseous medium rotationally fixed to the support plate, the rotary element being coaxial with said annular suction duct and defining a central supply duct having a central suction aperture, the internal diameter of said annular suction duct being substantially greater than the diameter of said central suction aperture, said rotor further comprising a circular collection casing coaxial with and at least partly covering the rotary element with the exception of said central suction aperture, the collection casing having, on its side nearer to said annular duct, a circular aperture whose diameter is at least equal to the external diameter of the annular duct.

2. Sampling apparatus according to claim 1, wherein a face of the collection casing at least partly covers the rotary element, said face being provided with a circular aperture centrally thereof, the diameter of said circular aperture being substantially smaller than the diameter of the central supply duct of the annular element, said circular aperture constituting the central suction aperture of the central supply duct of the rotary element.

3. Sampling apparatus according to claim 2, wherein the central annular suction duct leads into the collection casing opposite to the central opening provided in the face of said casing.

4. Sampling apparatus according to claim 1, wherein the central annular duct is defined within a tube communicating with said chamber by way of a bulb centrally located within said tube.

* * * * *

UNITED STATES PATENT AND TRADEMARK OFFICE
CERTIFICATE OF CORRECTION

PATENT NO. : 4,152,923
DATED : May 8, 1979
INVENTOR(S) : Paul COURBON

It is certified that error appears in the above—identified patent and that said Letters Patent is hereby corrected as shown below:

In the heading:

Item [73], change "Carbonnages de France" to

--Charbonnages de France--

Signed and Sealed this

Second Day of September 1980

[SEAL]

Attest:

SIDNEY A. DIAMOND

Attesting Officer     Commissioner of Patents and Trademarks